(12) United States Patent
Goldowsky

(10) Patent No.: US 6,527,699 B1
(45) Date of Patent: Mar. 4, 2003

(54) MAGNETIC SUSPENSION BLOOD PUMP

(76) Inventor: Michael P. Goldowsky, 7 Greenwood La., Valhalla, NY (US) 10595

( * ) Notice: Subject to any disclaimer, the term of this patent is extended or adjusted under 35 U.S.C. 154(b) by 0 days.

(21) Appl. No.: 09/980,264
(22) PCT Filed: Jun. 2, 2000
(86) PCT No.: PCT/US00/15240
§ 371 (c)(1),
(2), (4) Date: Nov. 27, 2001
(87) PCT Pub. No.: WO00/74748
PCT Pub. Date: Dec. 14, 2000
(51) Int. Cl.[7] ............................................. A61M 1/12
(52) U.S. Cl. ....................................... 600/16; 623/3.14
(58) Field of Search .................... 600/16–18; 623/3.13, 623/3.14

(56) References Cited

U.S. PATENT DOCUMENTS 5,928,131 A * 7/1999 Prem .......................... 600/16

* cited by examiner

*Primary Examiner*—Jeffrey R. Jastrzab
(74) *Attorney, Agent, or Firm*—Stanley J. Yavner

(57) ABSTRACT

This invention is a non-contact axial flow turbo blood pump for propelling blood, which is composed of a pump housing (24) that defines a pump axis, with inlet, outlet openings at opposite axial ends of the pump housing, a rotor unit (17) that defines a rotor axis, and opposing rotor axial ends. The pump magnetically suspends the rotor within the pump housing at the rotor axial ends so as to avoid causing physical contact between the housing to define fluid gaps between the rotor axial ends, and the magnetic suspension elements (13)(13').

44 Claims, 7 Drawing Sheets

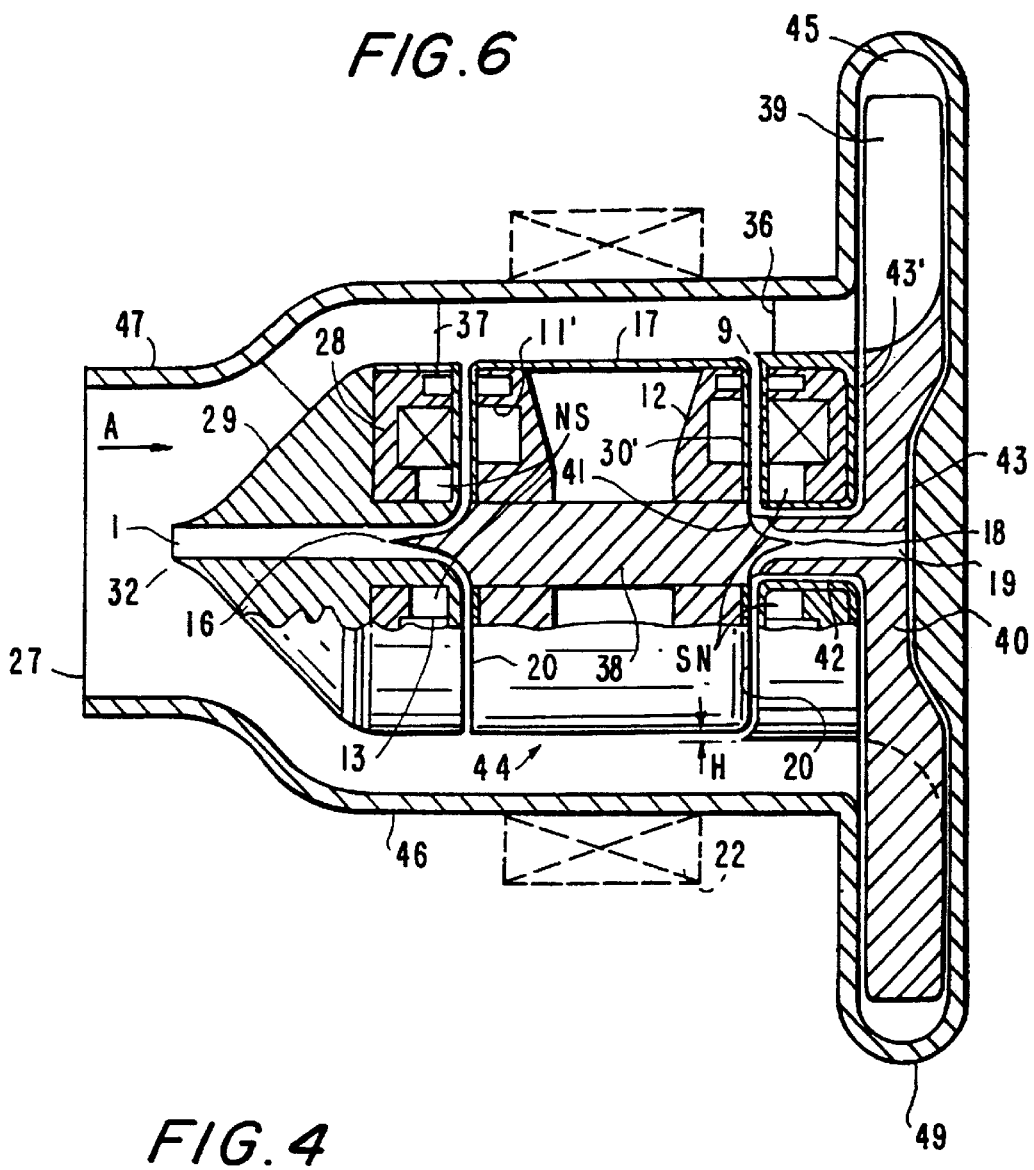
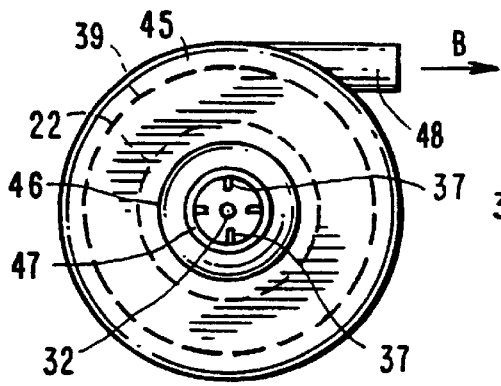
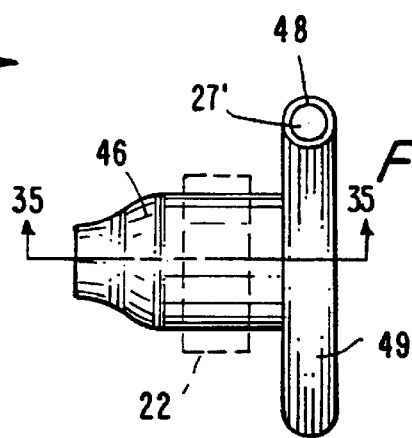

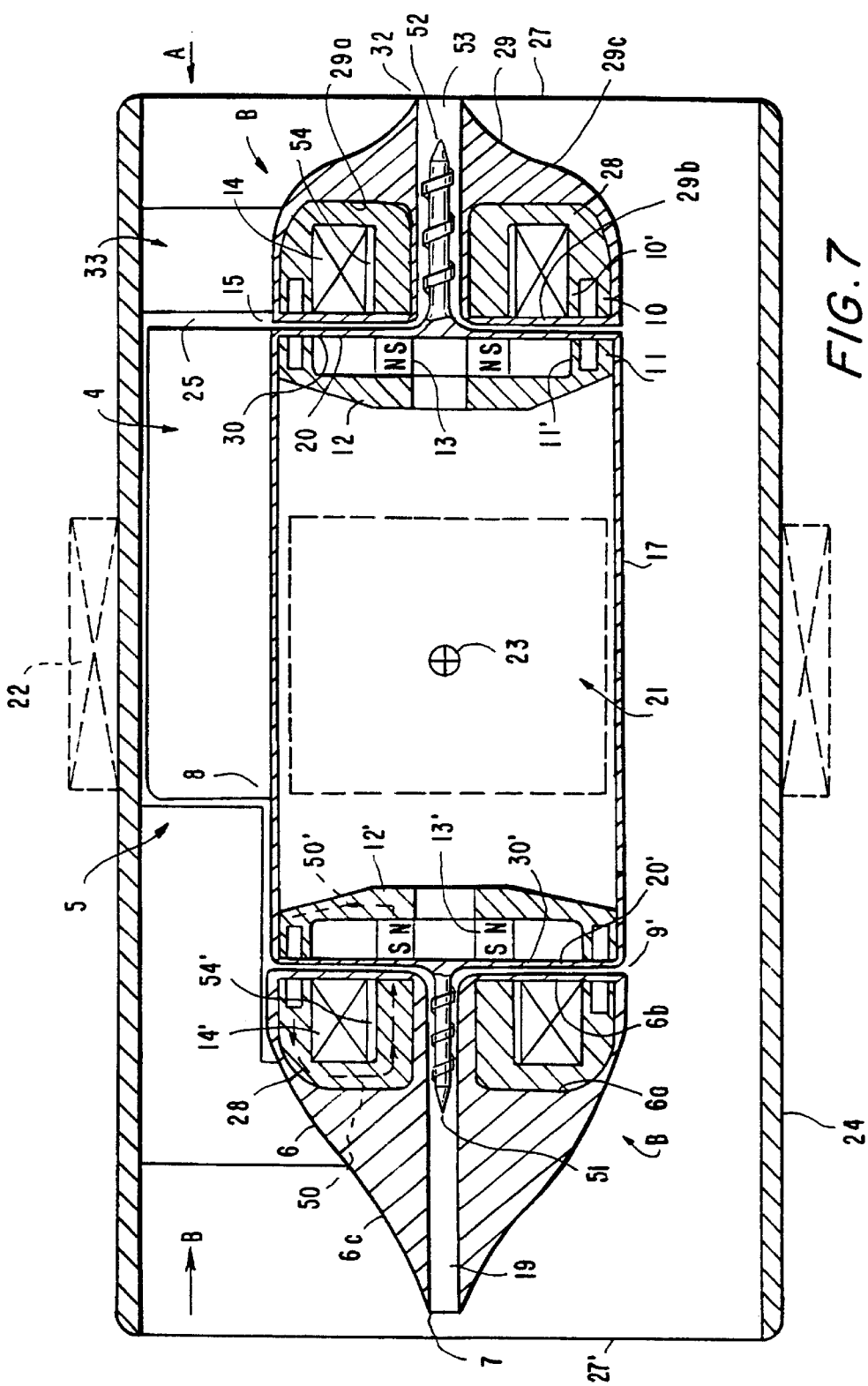

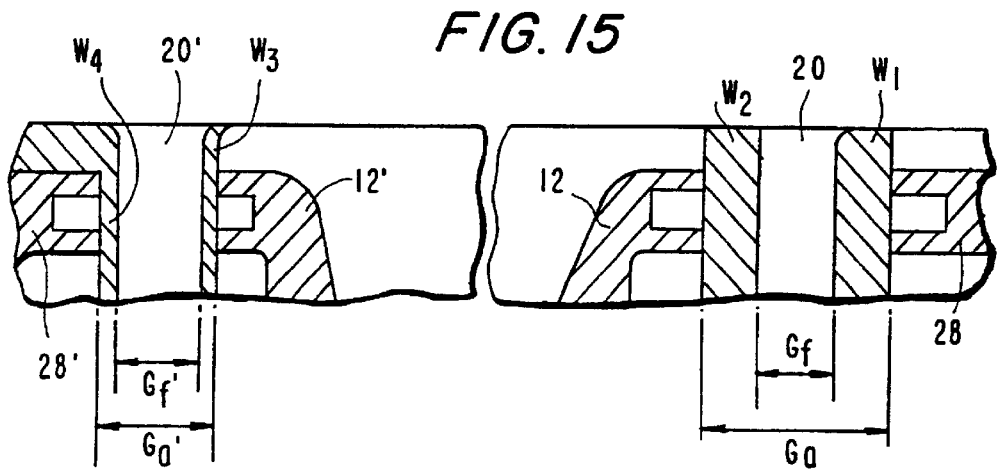
FIG. 15
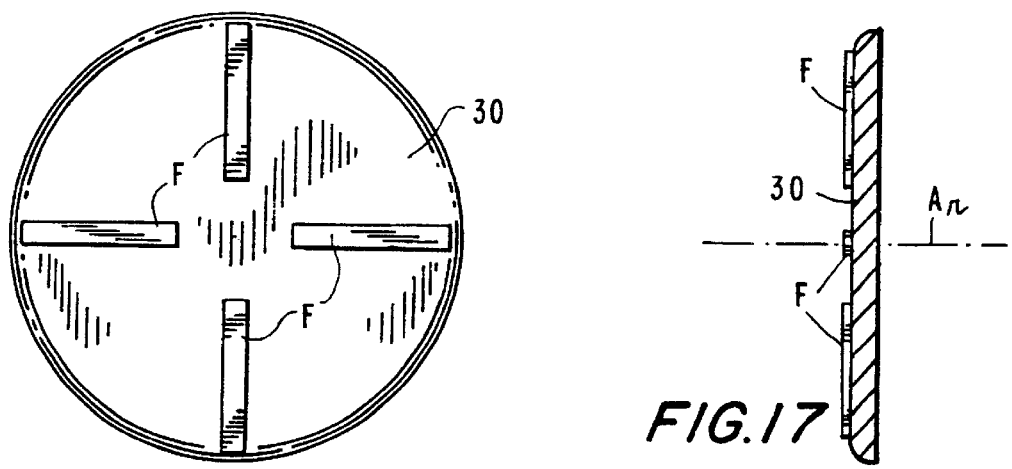
FIG. 16
FIG. 17
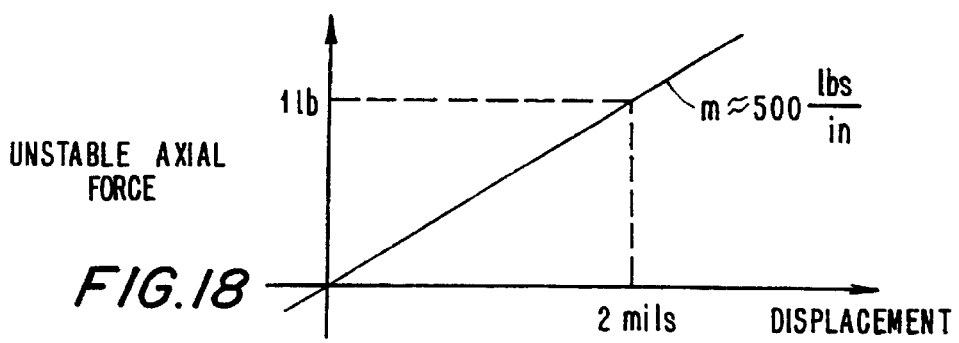
FIG. 18

MAGNETIC SUSPENSION BLOOD PUMP

BACKGROUND OF THE INVENTION

1. Field of the Invention

The present invention generally relates to rotary blood pumps that can be implanted into the chest of humans and can be used to assist a human heart in pumping blood, and, more specifically, to such blood pumps that use magnetic suspensions.

2. Description of the Prior Art.

The implantable blood pumps according to the latest technology that are now being developed to assist the heart are turbo pumps. They come in axial flow configurations, such as the Jarvik 2000; centrifugal configurations, such as one being developed by the Cleveland Clinic; and mixed flow types such as the "Streamliner" being developed at the University of Pittsburgh. All employ a high-speed rotary impeller rotating at thousands of rpm. Most, including the Jarvik 2000, use hard-contact journal bearings to support the rotor. Such use is not desirable because blood damage and thrombosis can be caused by the bearings. To try to circumvent contact-bearing problems, magnetic bearings are now being employed, as in the "Streamliner" pump. These are non-contacting bearings and result in minimal blood damage, since the bearing clearances can be kept large to reduce shear stress in the blood. However, the problem still exists of having to thoroughly wash out all the bearing clearances with fresh blood. This washout is essential to eliminate the formation of thrombus.

Magnetic bearings must be packaged in a small space in order to minimize the size of the pump, and this can be quite difficult. Most magnetic bearing pumps are too large and therefore unacceptable.

Another requirement for implantable blood pumps is low power consumption. Pumps that employ magnetic bearings are notorious for their power consumption, which can be-as high as 20 watts for just the bearings, 5 watts for the bearing(s) being more typical. The power delivered to the blood in a left ventricular assist device (LVAD)is about 3.0 wafts, so one does not want to expend more than 1.0 additional watt for the magnetic bearings.

Most magnetic bearings use permanent magnets or electromagnets to-generate radial magnetic fields that directly suspend the rotor radially. However, the bearing radial "stiffness" obtained using the relatively low air gap fields produced by the magnets is not high. A large bearing is, therefore, needed to hold imposed loads with small radial deflection.

Radially passive magnetic bearings are inherently unstable axially, as stated by Ernshaw's Law. Active axial control is, therefore, required to stabilize a rotor suspended by such bearings. Particularly for an axial flow turbo pump that has substantial axial forces acting on the rotor, the power consumed by the active coils can be unacceptably large. A "virtually zero power" (VZP) control loop is sometimes used to reduce power consumption. This control is generally known as VZP control and was first used back in the 1970s by J. Lyman, one of the founders of magnetic suspensions.

Implantable turbo blood pumps are typically run at constant rpm because it has been difficult to close the loop around the patient and physiologically vary pump flow rate according to the needs of the patient. By providing a base rate of flow, increased blood demand due to activity level is made up by the natural heart. However, a sick heart cannot make up much demand, and activity level is limited. Whatever cardiac output demand is made up by the patient's heart undesirably loads the sick left ventricle. To physiologically control pump output flow, extraneous sensors have sometimes been added to measure physiologic parameters of the patient. These have included the addition of blood pressure transducers to measure the pump outlet pressure or differential pressure. This is highly undesirable because the addition of extraneous sensors can cause thrombosis and long-term hemodynamic reliability concerns. A known LVAD uses an invasively placed series ultrasonic flowmeter to determine pump flow rate since the LVAD cannot directly measure its output blood pressure.

The natural heart produces pulsatile flow. Experiments have shown that this unsteady flow minimizes the onset of thrombosis in the larger arteries of the body because the flow pattern constantly changes. In a pulsatile flow pump, areas of stagnant flow are minimized or eliminated not only in the patient's arteries at the pump outlet, but within the pump itself. Current turbo pumps are direct current (DC) or steady flow devices that do not produce pulsatile flow. Even as the heart of a sick patient recovers and contributes some degree of pulsatile flow to the body, the degree of pulsatility is much less than that of the natural heart since the LVAD blood pump is unloading the sick heart. For "Bridge To Recovery" long-term implants, pulsatile flow from the LVAD is highly desirable.

SUMMARY OF THE INVENTION

Accordingly, it is an object of this invention.to provide alternate means to wash out the magnetic bearing gaps with fresh blood to eliminate thrombus formation at the bearings.

It is another object of the invention to allow bearing washout under minimal flow conditions through the pump.

It is still another object of the present invention to provide non-contact active washout means for the bearings.

It is yet another object of the present invention to provide a magnetic bearing geometry that is easily washed out by the blood flow to prevent areas of stasis.

A further object of this invention is to provide a small size bearing system that is simple in construction and packageable with the various turbo pump types for use with both adults and children.

A still further object of the present invention is to provide a control system that requires very low power when used with the disclosed high load capacity bearings.

It is yet a further object of the present invention to determine pump differential pressure in a direct manner without the addition of extraneous sensors.

It is an additional object of this invention to provide an active coil and magnet geometry that requires low power approaching zero to sustain axial loads.

It is still an additional object of the invention to provide safety of pulsatile flow by eliminating the undesirable condition of reverse flow through the pump.

It is yet an additional object of this invention to provide pulsatile flow in a reliable manner using pump differential pressure determined directly by the magnetic bearings.

It is also an object of this invention to shorten the length of an Archimedes screw type axial flow impeller by providing multiple parallel flow blades that minimally overlap. In mini-size blood pumps, for which this invention is intended, minimizing axial length of the pump is desirable particularly for applications in small women and children.

It is furthermore an object of this invention to provide a compact outlet stator of short axial length that does not damage blood while recovering impeller pressure.

In order to achieve the above objects, as well as others that will become evident hereafter, a blood pump in accordance with the present invention comprises a pump housing defining a pump axis, and inlet and outlet openings at opposite axial ends of said pump housing. A rotor is provided that defines a rotor axis and opposing rotor axial ends. Magnetic suspension means is provided within said pump housing at said rotor axial ends for magnetically suspending said rotor and passively maintaining the radial stability of said rotor so that said rotor axis remains substantially coextensive within said pump axis during operation. Control means is provided for maintaining axial stability of said rotor so that said rotor may absorb externally imposed axial loads and so that contact of said rotor within said pump housing is eliminated. Impeller means on said rotor operates to draw blood into said inlet opening and expel the blood through said outlet opening with rotation of said rotor. Drive means is provided for rotating said rotor and impeller means to thereby pump the blood, fluid gaps being formed between said rotor axial ends and said magnetic suspension means. Blood washout means is provided for continuously moving blood through said fluid gaps during rotation of said rotor to prevent formation of thrombus in said fluid gaps.

Preferably, the washout means provides positive or active flow of blood through fluid gaps where stagnation of blood might otherwise take place. In accordance with another feature of the invention, the drive means is arranged to drive the impeller means at a selected rotational speed, and means are provided for sensing the pressure differential within said pump housing and imparting a cyclic variation to said selected rotational speed of said drive means to provide pulsating movements of the blood through the pump and into the patient's circulatory system. Also, one structure for washout relies on generating differential pressures across the bearing gaps in a passive manner using the flow itself. An alternate structure attaches Archimedes screw pumps to the front and rear of the rotor to actively pump blood through the bearing gaps. In approximately 30% of heart-assist patients the natural heart re-conditions sufficiently after a year or two of LVAD use so that the pump is no longer needed. Rather than explant the device, the pump can be left in place and operated at minimal flow and power consumption. The active screw pumps allow proper bearing gap washout when the pump is put to sleep and minimally used.

An important feature of the invention is to mount the impeller means on a magnetically suspended rotor that is inherently stable in radial directions and to provide direct feedback signals useful for stabilizing the rotor in the axial direction. This feature substantially simplifies the design and construction of the pump, reduces its cost of manufacture and substantially enhances the reliability over extended periods of use.

A compact high radial stiffness magnetic bearing uses axial fringing ring magnetic fields to passively support the pump rotor radially. The flux is focused or concentrated from a permanent magnet in the fringing rings to produce very high radial load capacity in a small size. This is different than typical radially passive magnetic suspensions that employ radial magnetic fields. Active axial control stabilizes the bearing using a "Virtually Zero Power" control feedback loop. Low power and small size make the bearing applicable to axial flow and other configuration blood pumps particularly suitable for implantation. Differential pressure across the bearing fluid gaps, forcefully positively or actively washes the gaps with fresh blood to eliminate thrombus and flow stagnation. The rotor force on the magnetic bearings can be measured by the bearing control system. This allows the direct determination of differential pressure across the pump. This parameter can be used to obtain a pulsatile output pressure and flow and to exert physiological control on the pump output so as to match the patient's activity.

In the present invention; a very high radial stiffness bearing is obtained. This is accomplished by employing an axially directed fringing ring field that has a radial load capacity an order of magnitude higher than radially directed fields. This allows one to use a small diameter bearing that was not heretofore feasible. The high-load capacity results in low power consumption as well.

Until the present invention, it has not been possible to determine turbo pump differential pressure in a direct manner. Turbo pump differential pressure can be used in part to exert physiological control on the pump flow rate as demanded by the patient's activity level and heart rate.

BRIEF DESCRIPTION OF THE DRAWINGS

The invention, in accordance with preferred and exemplary embodiments, together with further objects and advantages, is more particularly described in the following detailed description taken in conjunction with the accompanying drawings, in which:

FIG. 4 is a front elevational view at the inlet end of a centrifugal type turbo pump in accordance with the invention, as viewed in the direction A in FIG. 6, employing the same magnetic bearings as in the axial flow pump of FIG. 1.

FIG. 5 is a side elevational view of the pump shown in FIG. 4, showing the impeller housing and flow outlet, and further showing the rotary motor stationary stator coils in dash outline.

FIG. 6 is a longitudinal section through the center of the housing of the pump shown in FIG. 5, the interior of the pump also being partially broken away to show the internal fluid flow passages in the pump, the impeller and its shaft being supported by two magnetic bearings without contact.

FIG. 7 is a view similar to FIG. 1, but shows two non-contacting Archimedes screws (unsectioned for clarity) attached to the rotor for actively moving the blood through the fluid flow gaps formed between the rotor axial end surfaces and the magnetic suspensions.

FIG. 15 is an enlarged section, partially broken away, of the magnetic bearing and rotor interface, showing the fluid flow gaps formed between the rotor and the magnetic bearing, and illustrating how the fluid flow gaps and air gaps may be modified at the upstream or inlet end with reference to the downstream or outlet end to compensate for average fluid forces acting on the rotor.

FIG. 16 is a side elevational view of an axial end surface of the rotor shown in FIG. 1, illustrating a plurality of radial vanes formed on the surface to provide positive or active centrifugal forces on the blood within the fluid gaps to force the blood to circulate within said gaps and prevent stagnation therein.

FIG. 17 is a side elevational view of that portion of the rotor shown in FIG. 16 and illustrating the radial vanes.

FIG. 18 illustrates the general linear relationship between axial instability force and axial displacement of the rotor from its, position substantially equidistant between the magnetic bearings.

DETAILED DESCRIPTION OF THE INVENTION

Figure 1:
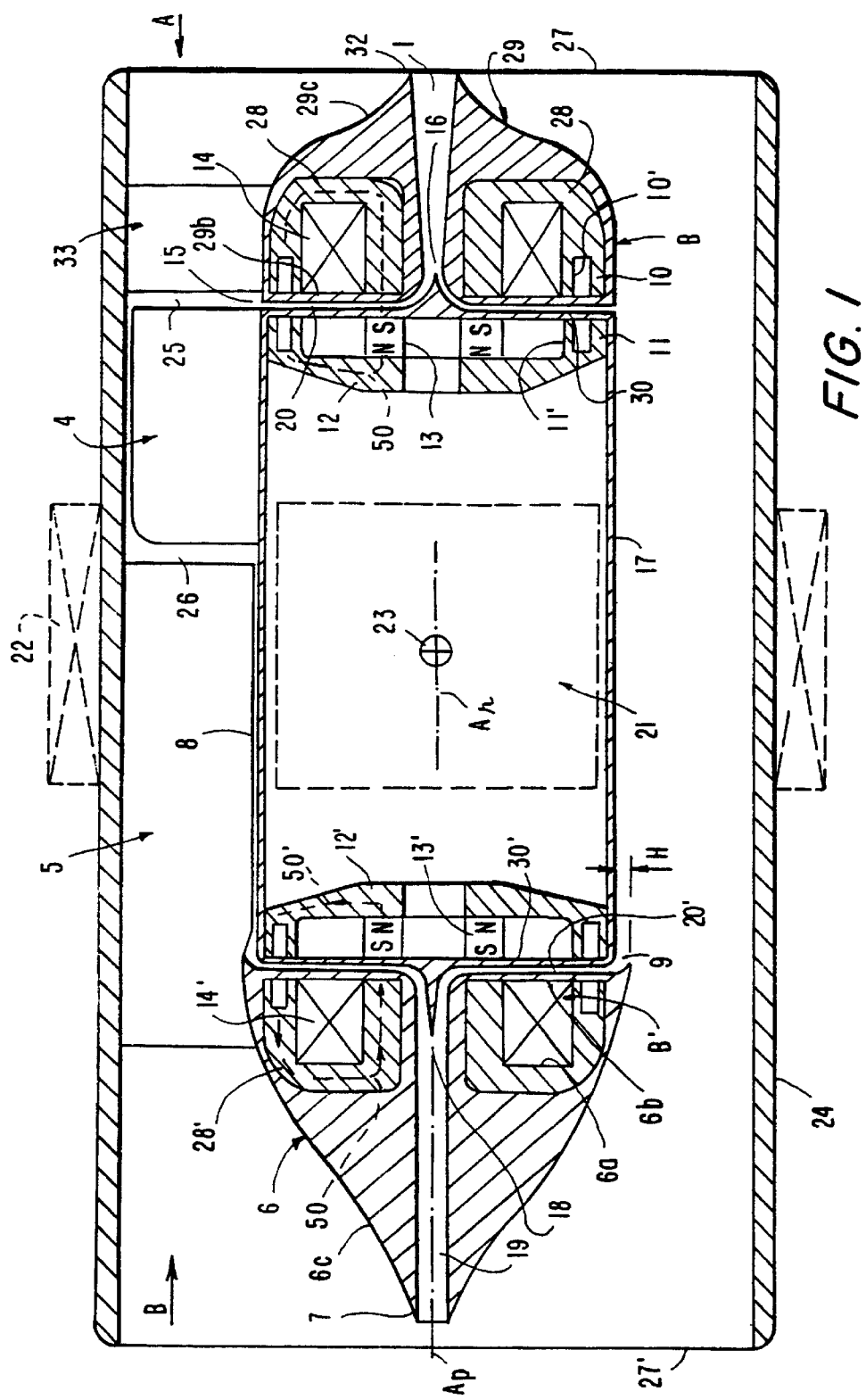
FIG. 1 is a longitudinal section through the center of the housing of an axial flow turbo pump embodying two magnetic bearings to suspend the rotor, the interior of the pump being partially broken away to show the internal fluid flow passages, the motor stator coils and rotor magnets being shown in dash outline.

In the following descriptions of axial flow and centrifugal flow pumps in accordance with the invention, the magnetic bearing configuration is the same, as well as other common elements such.as the fluid flow passages, magnetic circuits and the like. These common elements are assigned the same or primed identifying reference numerals throughout for consistency.

FIG. 1 illustrates an axial flow pump P that defines a pump axis $A_p$ and has a rotor R, having a rotor axis $A_r$, and a plurality of helically curved impeller blades 4 mounted for rotation about the pump axis $A_p$, as to be more fully described. The impeller blades 4 are attached to a rotor housing 17, which is made of thin-walled titanium for blood compatibility. All parts wetted by the fluid are typically titanium or any other suitable nonmagnetic material. Arranged at each axial end of the rotor R is a magnetic bearing pole piece 12, 12', which is iron or other high-saturation magnetic material. An annular permanent magnet 13, 13' is axially magnetized and co-axially positioned, between an associated pole piece 12, 12' and an axial end wall 30, 3' of the rotor R. The rotor R is formed of a cylindrical thin-walled titanium shell that hermetically seals the pole pieces 12, 12' in the rotor housing 17. The rotor housing 17 makes no physical contact with the stationary parts of the pump.

Magnetic bearings B, B' are provided at each axial end of the rotor R, a first half of which includes the magnets 13, 13' as well as the pole pieces 12, 12'. The second half Of the magnetic circuit for the magnetic bearings consists of iron yokes 28, 28', which are stationary. The paths of the magnetic flux 50, 50' are depicted in dash outline and are closed loops in,the plane show. The flux passes axially through fluid flow gaps 20, 20'. The yokes are sealed in the outlet fairing 6 and inlet fairing 29. Each fairing includes an annular region 6a, 29a for housing the yokes 28, 28' and active bearing coils 14, 14' proximate to the rotor. R, each annular region being sealed by walls 6b, 29b to define, with associated rotor axial end walls 30, 30', radial fluid flow gaps 20, 20'. The walls 6b, 29b are about 0.10-inch thick and made thin to minimize the dimension $G_a$ of the non-magnetic air gap. As best shown in FIG. 5, fluid flow gaps 20, 2' have a dimension $G_f$, this ranging from about 4 mils to 30 mils to keep the blood shear subhemolytic depending on maximum rotor rpm. While the fluid flow gaps 20, 2' at both axial lands of the rotor R should normally be approximately equal, the non-magnetic air gaps may be selected to have different values, as suggested in FIG. 15, in which the upstream air gap $G_a$ is greater than the downstream air gap $G_a'$, while both fluid flow gaps $G_f$, $G_f'$ are maintained to be about equal by changing the thickness of the walls $W_1$–$W_4$. It should also be clear that the same result can be achieved by maintaining the wall thickness the same, and the fluid flow gaps 20 the same, while physically displacing the pole pieces 12, 12' and selectively moving one or more of such pole pieces away from their associated walls to establish desired air gaps that are equal or different to compensate for average forces acting on the rotor during normal operation of the pump.

Figure 2:
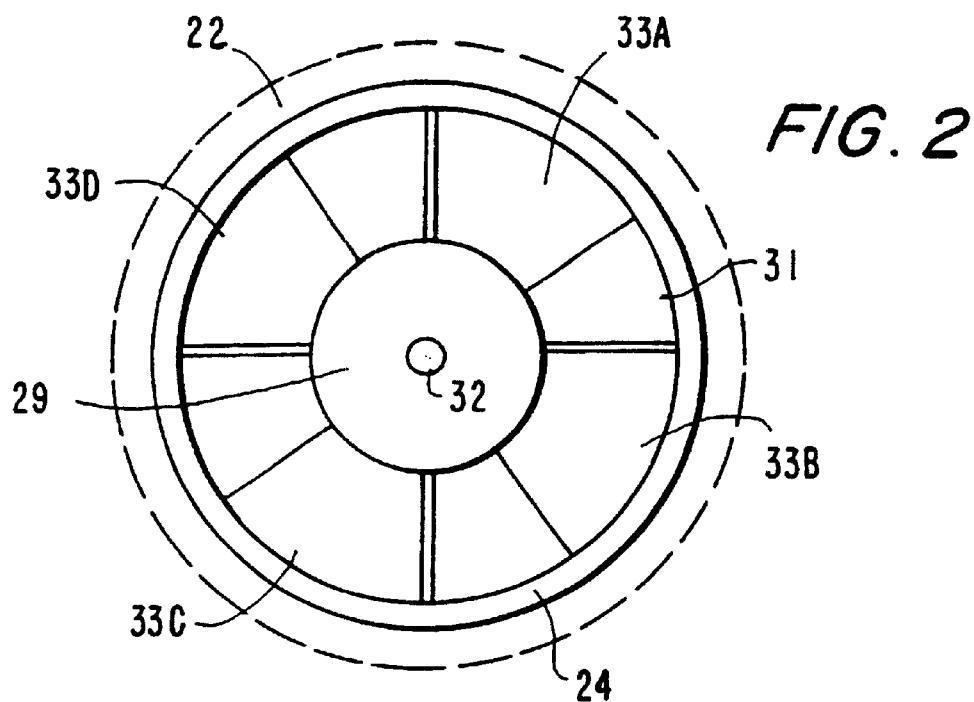
FIG. 2 is a front elevational view at the inlet end of the pump shown in FIG. 1, as viewed in the direction A.
Figure 3:
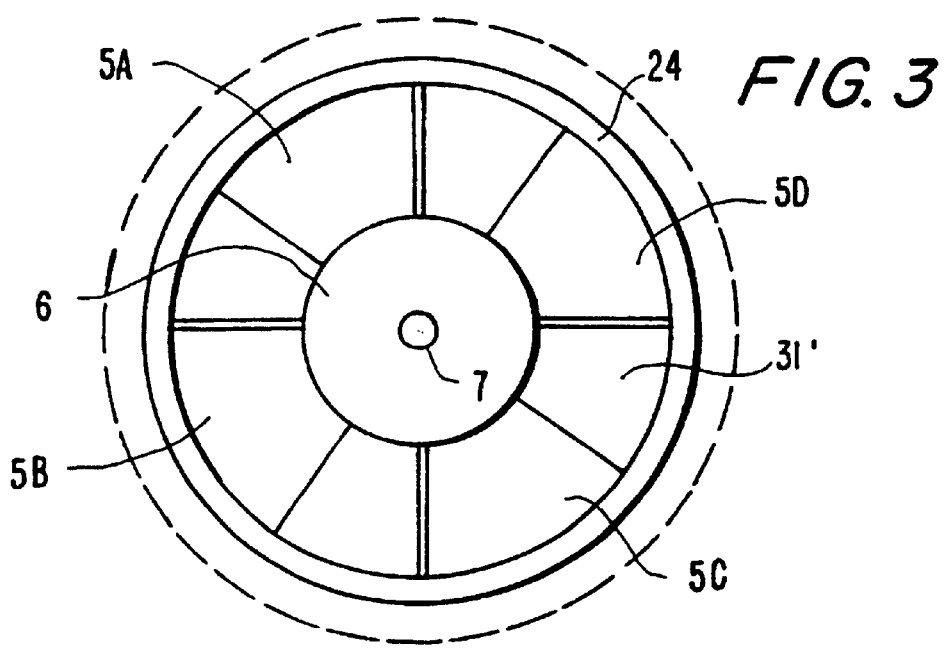
FIG. 3 is a rear elevational view at the outlet end of the pump shown in FIG. 1, as viewed in the direction B.

The inlet fairing 29 is radially outwardly tapered at 29c to provide streamlined flow without flow separation or turbulence. They attach to the pump housing 24 by means of inlet guide vanes 33. These vanes are generally straight or may be helically curved. Four curved vanes 33A–3D are shown in FIG. 2. Circumferential spaces 31 are formed between the inlet vanes. The end view of the inlet fairing 29 is visible in FIG. 2 as is its pointed tip 32. Similarly, the streamlined outlet fairing 6 is radially inwardly tapered, at 6c, and several equally spaced flow straightener vanes 5 hold outlet fairing 6 centered in the pump housing 17. A radial clearance 8 exists between the vanes 5 and the rotor housing 17. FIG. 3 shows four flow straightener vanes 5A–5D with circumferential spaces 31' between them as well as the pointed end 7 of the outlet.fairing 6.

Referring again to FIG. 1, and more particularly to the geometry of the two magnetic bearings, the yokes 28 and pole pieces 12 terminate at their outer diameters in two axially concentric and radially aligned thin fringing rings 10, 10' and 11, 11', respectively. Either one fringing ring or a plurality of such rings may be used. The radial stiffness and load capacity increase with the number of rings for a constant magnetic flux density in the air gaps. The axial magnetic field between associated opposing fringing rings is much stronger than the field in the permanent magnets 13, 13'due to the flux being concentrated across the narrow or radially thin fringing ring air gaps whose cross sectional area is less than that of the magnets 13, 13'. This creates a large passive radial load capacity or restoring force. However, the axial field creates an unstable axial stiffness or force when the rotor is not axially centered. This occurs when there are unequal air gaps at each end. A load on the rotor while it is pumping blood will create an axial force, which must be countered to keep the rotor from contacting the fairings 6, 29.

A transient counterforce is obtained by using active bearing coils 14, 14' which surround the inside diameter of the yokes. When currents flow through the coils superimposed magnetic fields are placed in series with the magnet flux, thereby modifying it. A clockwise current in the upstream bearing coil 14, as viewed along direction A in FIG. 1, increases the flux, while a counter-clockwise current decreases the flux. In this way the upstream bearing B can be made to attract the rotor R to the right, as viewed in FIG. 1, with greater force by increasing the air gap flux. The downstream bearing can, with a field decreasing current, be made to attract to the left with lesser force. This gives a net positive force to the right. Reversing both currents results in a net force to the left.

By utilizing a closed loop control system to control coil current based on an error signal of the axial position of the rotor, acceptably small axial movements of the rotor can be maintained. However, with an external pressure force on the rotor, power will be dissipated in the coils in order to counteract such external forces.

This bearing geometry also avoids this problem by allowing steady-state or slowly varying external forces to be countered or neutralized by the permanent magnets 13 instead of the coil by utilizing a different kind of control than position sensing. If the rotor is allowed to axially displace just the right amount, the bearing's axial instability force can hold the external load. The coil merely has to stabilize the axial position using a Virtually Zero Power (VZP) feedback loop. What this control loop does is drive the coil current to zero and the axial rotor velocity to zero in independent control loops. At the stable axial position under a load, the axial fringing forces are balanced with the load and the rotor will not move in either axial direction. In other words, rotor axial velocity will be zero and no DC current is required in either coil to hold a DC load.

A rotor axial velocity signal is needed to implement this VZP control scheme. The back emf voltage developed in at least one coil 14 can be used because it is directly proportional to rotor axial velocity and is stable over the long term with regard to direction. Thus, no added sensors are required to determine axial velocity.

To initially float a bearing that is axially touching, the axial force at the contacting end will generally be so great that the opposite coil will not have enough force capability to pull the rotor free. To solve this problem an initial DC current is momentarily placed in each coil to substantially buck out the flux from each magnet. This minimizes the axial instability force and allows the coils to be current controlled to center the rotor. Once the rotor is centered, the magnet bucking current can be reduced to zero.

A position control loop instead of a VZP loop can be used to initially float the bearing. To do this an axial position signal is needed. This can be obtained by measuring coil inductance by superimposing a low level AC current. Inductance is inversely proportional to magnetic circuit axial air gap. Thus, the coils 14 can also be used as a position sensor. Once the bearing is floated, control can be switched to the VZP mode. Periodically, over the life of the pump, this position control mode may be switched in momentarily to guarantee long-term stability of the axial position. This is a back-up and verifier for VZP control.

The axial flow pump in. FIG. 1 uses a constant diameter impeller blade 4 similar to the Jarvik 2000 axial flow pump. This constant diameter impeller is ideal for use with the disclosed magnetic bearing because the rotor can axially displace any amount in the constant diameter housing to hold a load as commanded by the VZP loop. Sufficient axial clearances 25, 26 and 20, 20' are used. Mixed flow turbo pumps on the other hand, have a radially tapered impeller along its length. The impeller fits closely in the tapered housing bore. Consequently, axial motion is much more limited to avoid contacting the housing, which limits the axial force capability of the bearing in the VZP mode.

The most critical goal of any blood pump design is to avoid areas of fluid stagnation for avoiding thrombus formation. Thrombus can initiate at flow stagnation points of zero velocity, particularly at surfaces or by regurgitant or reverse flow causing zones of near zero velocity. This has plagued magnetic bearing suspensions because totally suspending the rotor results in fluid spaces, gaps or passageways that are difficult to flush out with fresh blood. This problem is solved in the present invention by forcing the blood flow through these zones under pressure. Referring to FIG. 1, blood enters the pump along direction A. It enters a straight hole or a tapered hole 1 near stagnation pressure and, therefore, under high pressure. It flows to pointed pin diverter or deflector 16, where it is diverted radially into the fluid gap 20, which is a gap that separates the rotor and the stator. This flow is additionally sucked out at the gap outside diameter at 15 by the suction created at the inlet of rotary impeller 4, which is slightly downstream from the gap. This differential pressure creates a forced flow that washes out the gap 20.

Gap 20', at the outlet or downstream end of the rotor, is washed out with the assistance of a small circumferential lip or scoop 9 of radial height H, about equal in size to the gap 20', that forces some of the high velocity flow downstream of the impeller blades 4 to go radially into the gap 20'. High stagnation pressure exists at the scoop 9 relative to the exit pressure of conduit 19. This differential pressure actively washes out the being gap 20'. Pointed exit cone with sharp convergent point 18 blends the radial gap flow into the axial conduit 19 without a substantial stagnation point due to the sharp edge 18. To further reduce stagnation at tip or point 18, the tip can be located slightly off the center of rotation or pump axis. This eliminates stationary velocities. The tip deflector 16 at the inlet can also be located off center in relation to the pump axis with similar advantage.

Areas of reverse flow in the bearing clearances or fluid flow gaps 20, 20' have been eliminated in the disclosed design because unidirectional pressure differential exist across the left and right side gaps. This results in forced flow for unidirectional washout. Thus, no stagnant areas should exist, which should result in low probability of thrombus. The spinning rotor R also acts like an inefficient centrifugal pump tending to pump fluid radially outwardly at the gaps 20 and 20'. However, this effect is much weaker than the forced pressure flow, so that reverse flow is eliminated at the rear gap 20'. Radial flow is augmented in the front gap 20 by this centrifugal action. Referring to FIGS. 16 and 17, the efficiency in forcing the blood radially outwardly at the upstream gap 20 can be enhanced by providing suitably shaped radial fins F on the exterior surface of the axial end wall 30. These fins F project into the gap 20 a fraction of the gap width, on the order of several mils. Such fins F provide an active movement of the blood radially outwardly at the inlet gap 20. The specific sizes, shapes, orientations and/or positions of the fins for providing the specific desired results will be well known to those skilled in the arts.

An important feature of this invention is the magnetic bearing geometry with bi-directional active force capability and unique washout flow geometry that develops differential pressures. The rotary motor construction is known art using brushless motor technology, so it will not be described in detail. Permanent magnets 21 are located in the dotted zone 21 in the rotor. The rotor magnet's field interacts with the rotating magnetic field produced by the plurality of stator coils 22 surrounding the pump housing to create rotation torque when the coils are commutated. Further details are not given. However, it is noted that the side loads produced by the rotary motor should be minimized so as not to unduly load the magnetic bearings.

The disclosed bearing geometry uses two separate magnetic bearings B, B' that are spaced apart axially. This axial separation provides moment or cocking stability to the suspended rotor R. The rotor's center of gravity 23 as shown is ideally located at the approximate midpoint between the bearings. This imposes equal radial loads on the bearings from rotor weight or shock loads. Any motor radial forces are also equally shared.

Having thus described a preferred embodiment for axial and mixed flow turbo pumps, it will now be described how the same basic bearing design and washout differential pressures can be applied to centrifugal turbo pumps. In FIG. 5 a typical centrifugal pump includes a fluid flow exit opening 27' positioned tangentially to volute housing 49. The smaller diameter bearing housing 46 encloses the two magnetic bearings that support the rotor. The inside of the pump is shown in FIG. 5. Here only the bottom of the centrifugal impeller blade 39 is shown in section. The top blade is shown by taking a section between the blades. The spaced-apart magnetic bearings are of the same basic geometry previously disclosed except for one change, which is an alternate embodiment. The ring magnets 13 have been placed in the stator yoke instead of in the rotor pole. In this way they do not rotate, and are not subjected to centrifugal forces. The rotating iron pole piece 12 and the rotor R' can be more perfectly balanced and become simplified in construction. The magnetic bearing coils 14 now surround the magnet directly and equally well modify the magnet's flux as before.

The fluid flow direction is labeled by arrow A in FIG. 6. Blood impinges on inlet fairing 29 and enters conduit 1 as in the axial flow pump. It diverges radially at point pin 16 into the bearing fluid flow clearance 20. The static fluid pressure is higher at the edge 32 than at the exit of passage 20 because the fluid velocity is smaller here. This is guaranteed by choosing the cross sectional area of inlet passage 47 to be greater than that of annular passage 44 as calculable by Bernoulli's. Theorem. Gap 20 is forcefully washed out not only by this pressure differential but also by the remaining suction at gap 20 created by the centrifugal impeller 39, which has a plurality of radial blades. Fairing 29 is attached to the pump housing 46 using equally spaced thin vanes 37. The right or downstream side magnetic bearing yoke 28 at the outlet of the pump is held centered in the housing using outlet vanes 36 that may be straight or helically curved to optimally introduce fluid into the impeller vanes at their inside radius. Fluid is propelled radially outwardly by impeller vanes 39 and then enters the circumferential volute space 45, which communicates with fluid exit opening 27'.

The bearing axial gap 20 on the right or outlet side is washed out by directing a portion of the inlet flow radially into the gap by use of scoop 9, which extends above titanium rotor housing 17 by an amount H, previously discussed in connection with the axial flow pump. Although suction exists from the impeller at scoop 9, an equal suction exists at the root of impeller blade 39 inside centrifugal housing 49. Thus, this suction does not cause flow to take place through slot 20. The near stagnation fluid pressure at scoop 9 is high. At the trailing end of the gap that terminates in gaps 43 and 43', at the solid central portion of the impeller 39, the centrifugal force that is imposed by gap viscous drag will wash out gaps 43 and 43'. this creates an additional negative pressure at conduit 19. This differential pressure relative to the scoop 9 stagnation pressure forces flow down gap 20. Flow diverter 18 ensures smooth transition of radial flow to axial without stagnation points. The tip 18 can be located slightly off-center to eliminate stagnation at the tip. The asymmetric flow thus formed from an off-center tip in conduit 19 forms a vortex to wash out housing 49 adjacent conduit 19 where flow stagnation could otherwise occur. A plurality of channels 41 in the impeller shaft 38 permit communication between gap 20 and conduit 19. The impeller shaft 38 has a radial clearance 42 with the stationary bearing that is sufficiently large to prevent subhemolytic shear stress in the blood. Gaps 20, 43 and 43' are similarly sized. The shaft 38 is preferably made of titanium and is hermetically sealed to and supports pole pieces 12. All surfaces that contact the blood are preferably titanium in this and in the axial flow design. The titanium may have a biolite carbon or wear-resistant coating of titanium nitride or other coating to enhance bio-compatibility and gaulling resistance of bearing surfaces in the event of contact due to bearing failure or too large a shock load.

In the magnetic suspensions disclosed, the suspended rotor may touch down or contact the housing if a control system failure should occur. This makes the design failsafe so it can continue to function until replaced. To start up the bearing initially, the axial control system is energized first to eliminate contact. Then the rotor is spun up to the desired rpm.

Figure 8:
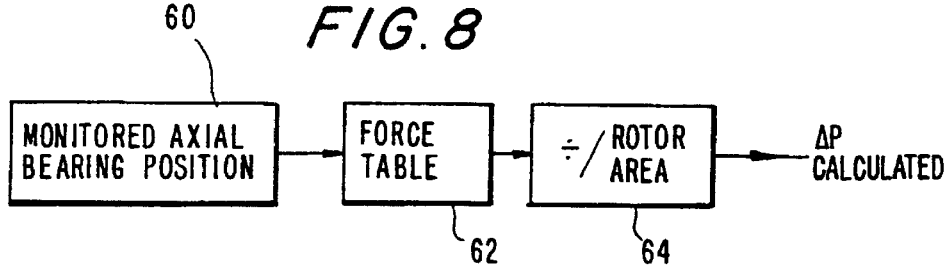
FIG. 8 is a block diagram of a circuit for calculating the transient or steady-state differential pressure across the rotor using the magnetic bearings as force sensors.

The magnetic bearings B, B' are, as noted, inherently axially unstable. That is why a VZP coil control system is needed. This instability force is used to good advantage to determine the axial force on the rotor. The differential pressure on the rotor is then calculated in a direct manner by dividing this force by the effective cross-sectional area of the rotor. This is shown in block diagram form in FIG. 8. The axial bearing position is monitored at 60, such as by measuring the coil inductance to determine the associate force. The desired differential pressure DP is calculated by dividing the derived force by the rotor area, at 64. In practice, a look up force table, which is useful for non-linear data, is not needed because the bearing force is sufficiently linear when large fringing ring blood gaps are used. See FIG. 18. To obtain transient force, the force contribution of the mass-inertia of the rotor is subtracted to provide the net external force.

As suggested, the inductance of the coils 14 in FIG. 1 can be used to monitor the rotor axial position. The coil electronics for determining rotor position can be simplified by using a separate small auxiliary position coil 54 (FIG. 7). Ideally, the coil 54 is wound beneath the main bearing coil 14, as shown in FIG. 7. While only a single position coil is needed, FIG. 7 shows a position coil 54 located in the inlet bearing B, while a redundant position coil 54' may be located in the outlet bearing B'. Less desirable is an added on or separate non-contacting ultrasonic or magnetic axial position sensor that would have to be integrated with the pump. Once pump differential, pressure is known, this information can be used to provide an accurate pulsatile flow as well as to provide a basis for physiologic control of the pump, in response to patient activity level.

Figure 9:
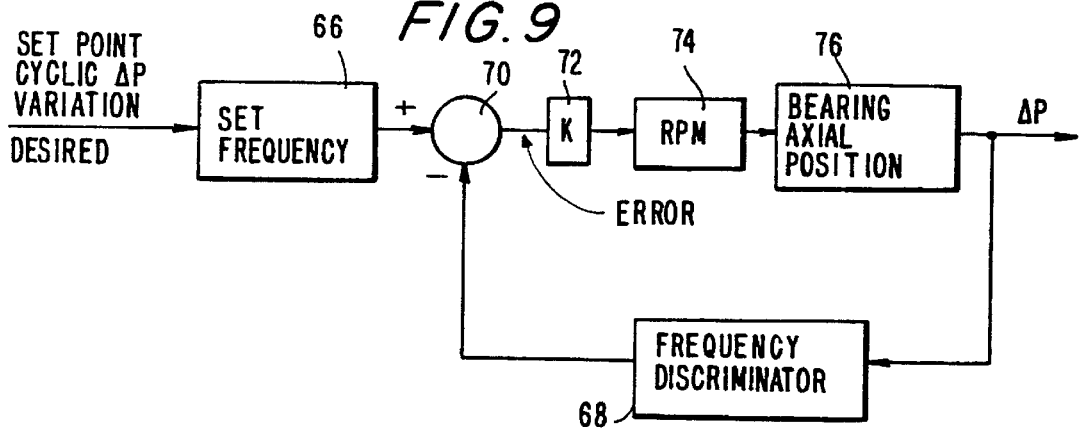
FIG. 9 is a block diagram of an electronic feedback system used to cyclically vary pump rpm in order to cyclically control pump differential pressure.

When used in a person, cyclically varying the pump rpm at a given frequency will cause the pump differential pressure to vary at the same frequency. Since the gage inlet pressure to the pump, when extracting blood from the heart, is relatively constant and low, being only several mmhg, differential pressure is a good measure of the much higher pump discharge pressure. Varying pump rpm instantaneously varies pump flow rate, which changes outlet pressure to the body (when discharging into the aorta, for example). Pump differential pressure is monitored by the bearings. Any error in pump differential pressure amplitude is corrected by a feedback loop which fine tunes the pump rpm until the desired pressure variation is obtained. This is shown schematically in the control system of FIG. 9. In FIG. 9, the desired cyclic differential pressure variation is input as well as by setting a cyclic frequency, at 66. A frequency discriminator 68 separates the pump's differential pressure variation from that produced by the beating of the natural heart at a different frequency. The differential pressure amplitude across the pump is compared to the set point differential pressure at comparator 70. An error signal at the output of the comparator is input to.a proportional amplifier 72 having a selected gain K to control the drive motor rpm 74, which, in turn, reflects variations in rotor axial position, at 76, due to the associated variations in pressures.

A typical or normal set point pressure variation is 120/80. This means that during the pump cycle, blood pressure reaches a maximum of 120 mmhg (systolic pressure) and a minimum of 80 mmhg (diastolic pressure). By being able to achieve accurate systolic and diastolic pressures, flow reversal through the pump is avoided and an invasive flowmeter or other sensor is not needed. The proportional gain labeled "K" provides the desired sensitivity of control to give a stable and accurate aortic pressure.

Physiologic control of pump flow rate is now possible based on differential pressure. If, for example, the patient's exercise level increases, his or her average blood pressure will decrease, due to a decrease in peripheral resistance with exercise, if cardiac output is not increased. Therefore, pump average rpm is merely increased in a feedback loop until the desired average blood pressure is maintained, which is typically 100 mmhg. This will automatically increase LVAD flow rate in order to maintain a constant average aortic pressure.

The patient's own heart rate can also be used as a parameter to set the average aortic pressure as well as the desired systolic/diastolic ratio. The patient's own heart rate may be monitored electrically as is done in pacemaker devices. However, this is undesirable because of the need to introduce heart monitoring electrodes. With the present invention the patient's:heart rate can be directly monitored instead by analyzing the frequency content of the force on the magnetic bearings. If the cyclic variation in pump rpm (that produces pulsatile flow) is done at a frequency somewhat different from that of the natural heart, the heart's blood-pressure frequency can be extracted from the total differential pressure signal. Average pump output pressure can then be made proportional to the patient's heart rate which is a known physiological function. The same type of feedback loop can be used as in FIG. 9.

Thus, one can monitor the output pressure of the natural heart itself and how well the natural heart is pumping and recovering over time. One can wean a patient with a recovering heart off the LVAD by reducing LVAD flow contribution if desired. Having heart and pump individual pressure data serves as a performance monitor. This is a major advantage for a long-term implantable device.

In the event that it is desired that the flow rate through the LVAf be substantially reduced—for example, in patients that can be weaned therefrom—we need to still guarantee full washout of the bearing gaps 20 shown in FIGS. 1 and 7. Referring to FIG. 7, helical deep groove screw pumps are attached to each end face of the rotor R. The inlet screw item 52 and outlet screw 51 both pump fluid, toward the impeller and away from it respectively. The screw outside diameter has a clearance so that it does not contact the ho using during normal operation. In the event of radial shock transient loads that cannot be sustained by the magnetic bearings, the screws are to contact the housing as mechanical back-up bearings. Wide axial lands on the e screw thread outer diameter provide low contact stress bearing areas for this purpose. The flow that is actively pumped through the bearing gaps 20, 20' by the screws 51, 52 is sufficient so that one need not rely on pump-flow rate to generate differential pressures s for washout. This can be applied to the centrifugal pump con figuration in FIG. 6 as well.

The scoop 9 in FIG. 1 at the outlet bearing gap 20' has been eliminated in FIG. 7 since screw pump 51 will produce sufficient flow without it. The option to eliminate the scoop, if desired, provides flexibility in design to eliminate thrombus formation at this location. The pointed tips of the screws 51 and 52 may be radially offset from the pump axis $A_p$ to avoid zones of blood stagnation at the tips.

Figure 10:
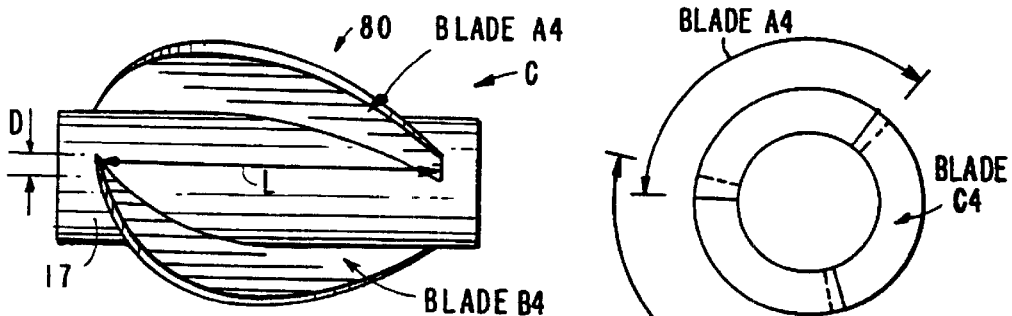
FIG. 10 is a side elevational view of an axial flow three-blade impeller, with only two blades in view, emanating from a central hub.

FIG. 10 depicts an improved axial flow Archimedes screw impeller 80 for the blood pump that uses multiple short blades. A basic or conventional Archimedes screw pump (originally invented by the ancient Greek Archimedes for low-pressure crop irrigation use) consists of a single screw thread of several turns. At least one complete 360-degree turn is needed to minimize back leakage in these pumps when substantial pressures have to be generated as in implantable blood pumps. To obtain one complete turn at shallow helix angles in particular, the screw thread axial length becomes quite long. A long length impeller cannot fit in a mini-size axial flow pump as taught in the present invention. Therefore, the impeller length L has to be reduced.

It has been verified with prototype testing by the inventor that an equivalent hydraulic efficiency Archimedes screw can be made that is substantially shorter in overall length by using multiple short blades around the circumference. The more blades that are used, the shorter is the length. These blades have the same helix angles as a single long screw to give similar performance. Because multiple blades are used that partially overlap, back leakage flow through the impeller is identical to that of a single 360 degree one-turn screw of longer length. This has been experimentally verified.

Due to the finite transverse thickness of the blades, the addition of too many blades results in a reduction of open flow area between the blades. This decreases flow rate and undesirably increases blood shear stress at a given flow rate. This can cause hemolysis. For this reason, the minimum number of blades needed to achieve the desired result with an acceptably short axial length is ideal. A two-blade impeller decreases axial length to half, a three blade to a third and a four blade to a fourth, with diminishing returns beyond four blades.

Figure 11:
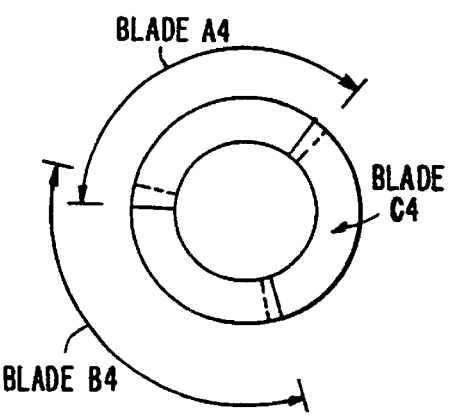
FIG. 11 is an end view of the impeller shown in FIG. 10, showing all three blades, which are round at their outer diameters, as viewed along direction C in FIG. 10.

Blade overlap D in FIG. 10 may be zero up to ideally several degrees of circumference. This eliminates a straight through line of sight fluid leakage path that would otherwise exist between the trailing edge of one blade and the leading edge of an adjacent blade. Existence of this back leakage path would substantially lower impeller efficiency. In other words, if clearance D is negative, excess leakage will occur at high pressures resulting in poor pump efficiency. In a preferred prototype a three-blade impeller of 0.80 in O.D. uses blades of 0.90 in. in length with 10 degrees of overlap D. FIG. 11 shows these blades as A4, B4 and C4 in end view. For the three blades shown, each extends 120 degrees+10 degrees overlap=130 degrees.

An Archimedes screw pumps fluid by the pushing action of the advancing screw helix on the fluid in the surrounding housing and produces no lift. An airplane or ship propeller does not operate this way because it relies on the lift produced by the blades and there is no enclosed housing used. Overlapping the blades is not taught in the design of these propellers. This is particularly evident in two-blade propellers where the propellers are located 180 degrees apart and there is a large clearance between the blades. A lift generating propeller is a satisfactory design for these applications because high pressures are not generated in ship or aircraft propulsion, unlike in blood pumps.

Figure 12:
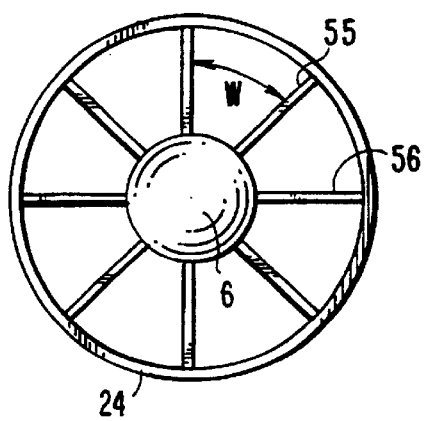
FIG. 12 is an end elevational view of an outlet end of the vane geometry that forms an outlet diffuser in an axial flow configuration, similar to the one shown in FIG. 1.
Figure 13:
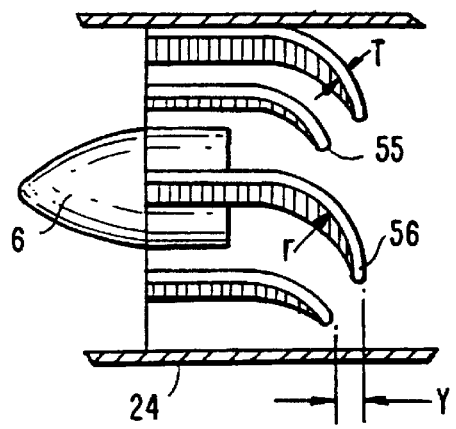
FIG. 13 is a side elevational view of the vanes shown in FIG. 12 with the cylindrical housing in cross section.

FIGS. 12 and 13 illustrate a novel exit stator or diffuser that is designed to redirect the substantially tangential flow off the impeller into axial flow for discharge at the pump outlet. The vanes are curved almost 90 degrees. Flow enters nearly tangentially. The flow cross sectional area between vanes at the entrance into the diffuser is kept approximately the same at the impeller exit. This matches blood flow velocity for minimal blood cell trauma at the diffuser entrance. The rotational kinetic energy of blood exiting the impeller is converted into static pressure as flow traverses in the ever-increasing flow area between vanes. Minimum flow velocity exists at the diffuser exit where flow is all axial.

It is essential to accomplish tangential-to-axial flow redirection without flow separation on the back surface of the vanes. Otherwise, blood damage and thromboemboli from turbulence can occur. This is accomplished by interposing shorter auxiliary vanes 55 between primary curved vanes 56. These auxiliary vanes 55, which do not exist at the vane entrance, are set back a distance Y. The absence of the vanes 55 at the inlet or front of the diffuser provides the extra circumferential space needed to obtain the desired flow cross-sectional area for flow velocity matching. This is essential because the finite thickness T of the primary vanes requires a substantial space in such a small diameter mini-size pump. The resulting narrower spacing between vanes where secondary vanes 55 are added is intended to be at the onset of the more highly curved portion of the primary vanes where flow separation tends to initiate. The narrower gap W forces the flow to hug the wall on the downstream convex surface of the vanes, thereby minimizing flow separation.

It is also desirable to minimize the number of vanes in order to reduce the surface area in contact with blood for minimizing thrombosis. Proper choice of vane thickness T can creates the desired average channel width W for a given number of vanes. In a preferred embodiment eight relatively thin vanes are used.

Flow separation is also reduced by using as large a radius of curvature "r" as possible for the vanes as shown in FIGS. 12 and 13. However, a larger radius creates a longer axial length for the diffuser. In a mini-pump along axial length is undesirable. A shorter axial vane with small radius of curvature "r" can be employed without flow separation by using a smaller channel width W, provided blood shear stress remains acceptably low. In a preferred embodiment, minimal flow separation exists when W ranges from the 0.10 to 0.40 in and the radius of curvature "r" falls within practical size limits of 0.30 to 1.25 in.

Referring to FIG. 7, the impeller 4 is shown to have a longer axial length than in FIG. 1. An advantage of this configuration is that the motor armature magnets, which are located in dotted box 21, are completely located beneath the impeller blades. Since the impeller and magnets rotate together, no eddy currents are generated in the blades due to rotor rotation. This is not the case in FIG. 1 where a very short impeller is shown. In this configuration eddy currents will be dissipated in the stationary outlet stator blades because they are located in the field above the rotating magnets. This will increase motor power consumption.

Figure 14:
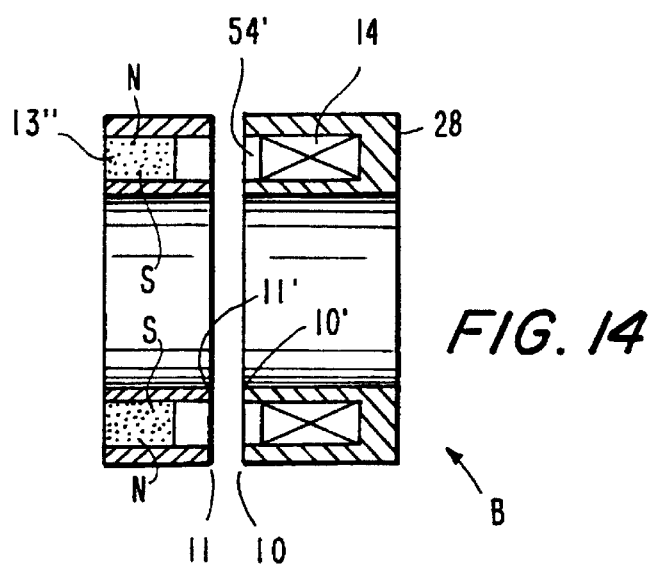
FIG. 14 is a partial cross sectional view of an alternate, very compact fringing ring magnetic bearing construction that employs a radially magnetized magnet rather than an axial one.

Referring to FIG. 14, an alternate embodiment of the fringing ring magnetic bearing will be discussed because it offers additional advantages. A longitudinal section through the bearing B is shown in FIG. 14. A radially magnetized magnet 13" is employed and located between the circular fringing rings 11 and 11'. The magnet ring may be composed of a plurality of radially magnetized pie-shaped sections or it can be radially magnetized in one piece. The bearing's axial instability force is only due to the air gap flux of the fringing rings. The magnet produces no instability force since its field is contained in the iron. So the one advantage of this configuration is its reduced axial instability force compared to the axially magnetized magnets of the type shown in FIG. 1. Also, the inside diameter of the bearing is now substantially open space, allowing more compact incorporation in smaller pumps for use with children.

While this invention has been described in detail with particular reference to preferred embodiments thereof, it will be understood that variations and modifications will be effected within the spirit and scope of the invention as described herein and as defined in the appended claims.

What I claim:

1. A blood pump to propel blood therethrough, comprising:
   a pump housing defining a pump axis, and inlet and outlet openings at opposite axial ends of said pump housing;
   a rotor defining a rotor axis and opposing rotor axial ends;
   magnetic suspension means within said pump housing at said rotor axial ends for magnetically suspending said rotor without physically contacting said housing and defining fluid gaps between said rotor axial ends and said magnetic suspension means and substantially maintaining the radial stability of said rotor so that said rotor axis remains substantially coextensive with said pump axis during operation;
   control means for maintaining axial stability of said rotor so that said rotor may absorb eternally imposed axial loads and maintain said fluid gaps and axial separation between said rotor and said pump housing;
   impeller means on said rotor operative to draw blood into said inlet opening and expel the blood through said outlet opening with rotation of said rotor;
   drive means for rotating said rotor and impeller means thereby pumping blood; and
   blood washout means for continuously moving blood through said fluid gaps during rotation of said rotor to prevent formation of thrombus in said fluid gaps.

2. A blood pump as defined in claim 1, wherein said rotor comprises a cylindrical rotor housing formed of a cylindrical wall coaxial with said rotor axis and non-magnetic circular transverse walls at each axial end.

3. A blood pump as defined in claim 2, wherein said cylindrical and transverse walls are sealingly attached to each other to seal the interior of said rotor housing.

4. A blood pump as defined in claim 1, wherein said magnetic suspension means includes magnetic field generating means for establishing axially directed fields across said fluid gaps at each axial end of said rotor.

5. A blood pump as defined in claim 4, wherein said suspension means includes a support member at each axial end of said rotor and arranged along said pump axis generally centrally within said pump housing and spaced predetermined axial distances from said rotor to form said fluid gaps, at each axial end of said rotor, that extend between said pump axis and the radially outermost region of said rotor.

6. A blood pump as defined in claim 5, wherein said support members comprise inlet and outlet fairings configured to produce a streamlined outline and reduce flow turbulence and separation at said inlet and outlet openings, respectively.

7. A blood pump as defined in claim 5, wherein each of said support members encloses an active bearing coil for creating at least one component of said axially directed fields and a permanent magnet within each axial end of said rotor to create a second component of said axially directed fields across said gaps.

8. A blood pump as defined in claim 7, wherein each active bearing coil is associated with a magnetizable yoke through which said axially directed fields flow, each yoke being arranged to cause said axially directed fields to extend across said fluid gaps in line with the circumferential peripheries of said rotor axial ends.

9. A blood pump as defined in claim 8, wherein pole pieces are provided at each axial end of said rotor cooperating with an associated permanent magnet to direct said second components of said axially directed fields proximate to said peripheries of said rotor axial ends.

10. A blood pump as defined in claim 9, wherein said pole pieces and yokes include magnetizable portions that are axially spaced across associated fluid gaps, said magnetizable portions being formed as radially spaced substantially concentric fringing rings having cross-sectional areas in radial planes that are less than the cross-sectional areas of said permanent magnets to increase the magnetic flux density bridging said fluid gaps between associated radially opposing fringing rings.

11. A blood pump as defined in claim 7, wherein said permanent magnets at each axial end of said rotor defines a magnetic axis substantially coextensive with said pump housing and rotor axes.

12. A blood pump as defined in claim 7, wherein each permanent magnet at each axial end of said rotor is radially magnetized.

13. A blood pump as defined in claim 5, wherein each of said support members encloses an active bearing coil for creating one component of said axially directed fields and a permanent magnet to create a second component of said axially directed fields, a magnetizable yoke being arranged attach axial end of said rotor to provide a return path for said axially directed fields within said rotor.

14. A blood pump as defined in claim 1, wherein said fluid gaps are dimensionally substantially equal at both axial ends of said rotor to allow substantially equal flow of blood and washout at both axial ends of said rotor.

15. A blood pump as defined in claim 1, wherein said washout means for washing out said fluid gap at said inlet opening includes an inlet axial hole arranged substantially along said pump axis and opening in the direction of said inlet opening at one axial end and being in fluid flow communication with an associated fluid gap at the other axial end, whereby at least some of the blood flowing into said inlet opening is directed and caused to flow through said inlet axial hole and though said associated fluid gap.

16. A blood pump as defined in claim 15, further comprising means for preventing stagnation of blood within said inlet axial hole.

17. A blood pump as defined in claim 16, wherein said stagnation preventing means comprises an element projecting from said rotor at least partially into said inlet axial hole to move the blood therein with rotation of said rotor.

18. A blood pump as defined in claim 17, wherein said element is mounted eccentrically in relation to said rotor axis.

19. A blood pump as defined in claim 1, wherein said washout means for washing out said fluid gap at said outlet opening comprises an outlet axial hole having one axial end in fluid flow communication with a fluid gap at said outlet end and opening in the direction of said outlet opening at the other axial end of said outlet axial hole; and diverting means for diverting at least some of the blood caused to flow through said pump housing by said impeller means into said associated fluid gap, whereby blood flows through said fluid gap at said outlet opening and expelled through said other axial end into said outlet opening.

20. A blood pump as defined in claim 19, further comprising means for preventing stagnation of blood within said outlet axial hole.

21. A blood pump as defined in claim 20, wherein said stagnation preventing means comprises an element projecting from said rotor at least partially into said outlet axial hole to move blood therein with rotation of said rotor.

22. A blood pump as defined in claim 21, wherein said element is mounted eccentrically in relation to said rotor axis.

23. A blood pump as defined in claim 1, wherein said blood washout means includes at least one projection mounted on said rotor projecting into said fluid gap, whereby said projection enhances centrifugal flow of blood with rotation of said rotor.

24. A blood pump as defined in claim 23, wherein said at least one projection is in the form of at least one substantially radial fin.

25. A blood pump as defined in claim 24, wherein a plurality of radial fins are provided on said rotor projecting into said fluid gap at said inlet opening, said radial fins being angularly spaced from each other about said rotor axis.

26. A blood pump as defined in claim 1, wherein said rotor comprises a generally cylindrical rotor housing having a cylindrical wall defining an axis coextensive with said rotor axis and an outer cylindrical surface forming, with said pump housing, an annular passageway for the blood in moving from said inlet to said outlet openings, and said impeller means comprises a plurality of axially directed helical blades mounted on at least an axial length of said outer cylindrical surface, said blades being substantially equally angularly spaced from each other about said rotor axis and said helical blades having a pitch and a length to at least partially circumferentially overlap as viewed along said rotor axis to minimize back leakage.

27. A blood pump as defined in claim 26, wherein three helical blades are provided each extending a total of 130° about said rotor axis to provide a 10° overlap with adjacent helical blades.

28. A blood pump as defined in claim 1, wherein said control means includes active bearing coils forming part of said magnetic suspension means arranged to detect variations in axial positions of said rotor, and means for establishing differential pressure acting on said rotor on the basis of said variations.

29. A blood pump as defined in claim 32, wherein said control means includes a "virtually zero power" (VZP) control feedback loop for axially stabilizing said rotor on the basis of the detected axial velocity of said rotor and coil current.

30. A blood pump as defined in claim 1, wherein said pump housing and impeller means are arranged to pump the blood axially between said inlet and outlet openings.

31. A blood pump as defined in claim 1, wherein said pump housing and impeller means are arranged to expel the blood centrifugally radially.

32. A blood pump as defined in claim 1, wherein said control means includes means for applying a desired cyclic differential pressure variation on said rotor to cause pulsatile flow of blood through the pump.

33. A blood pump as defined in claim 32, wherein said control means includes means for setting frequency of pulsatile flow and a feedback loop for comparing selected set frequency and differential pressure with the variations detected as a function of the axial position of said rotor.

34. A blood pump as defined in claim 1, wherein said pump housing and impeller means are arranged to provide axial flow of blood, and further comprising tangential-to-axial flow redirection means for redirecting the tangential flow of blood resulting from rotation of said impeller means to axial flow at said outlet end to eliminate turbulence and flow separation at said outlet end.

35. A blood pump as defined in claim 34, wherein said flow redirection means comprises a plurality of curved vanes at said outlet end, alternate curved vanes having different axial lengths providing extra circumferential space needed to obtain desired flow cross-sectional area for flow velocity matching at the entrance to flow said redirection means.

36. A blood pump as defined in claim 1, wherein said drive means includes a permanent magnet arranged generally axially centrally within said rotor to define a center of gravity of said rotor, and stator coils on said pump housing generally axially aligned with said center of gravity, whereby equal radial loads can be imposed at said magnetically suspended axial ends.

37. A blood pump as defined in claim 1, wherein said blood washout means includes means for actively moving said blood through fluid gaps during rotation of said rotor.

38. A blood pump as defined in claim 37, wherein said blood washout means includes at least one Archimedes screw for diverting blood at said pump inlet opening and forcing the diverted blood to flow through the fluid gap at said inlet opening.

39. A blood pump as defined in claim 37, wherein said blood washout means includes at least one Archimedes screw for actively removing blood from said fluid gap at said pump outlet opening and directing such removed blood to pump outlet opening.

40. A blood pump to propel blood therethrough, comprising:

a pump housing defining a pump axis, and inlet and outlet openings in said pump housing;

a rotor defining a rotor axis and opposing rotor axial ends;

suspension means within said pump housing at said rotor axial ends for suspending said rotor for rotation within said housing and defining fluid gaps between said rotor axial ends and said suspension means and substantially maintaining the radial stability of said rotor so that said rotor axis remains substantially coextensive with said pump axis during operation;

control means for maintaining axial stability of said rotor so that said rotor may absorb externally imposed axial loads and maintain said fluid gaps and axial separation between said rotor and said pump housing;

impeller means on said rotor operative to draw blood into said inlet opening and expel the blood through said outlet opening with rotation of said rotor;

drive means for rotating said rotor and impeller means thereby pumping blood; and blood washout means for continuously actively moving blood through said fluid gaps during rotation of said rotor to prevent formation of thrombus in said fluid gaps.

41. A blood pump to propel blood therethrough, comprising:

a pump housing defining a pump axis, and inlet and outlet openings in said pump housing;

a rotor defining a rotor axis and opposing rotor axial ends;

suspension means within said pump housing at said rotor axial ends for suspending said rotor for rotation within said housing and defining fluid gaps between said rotor axial ends and said suspension means and substantially maintaining the radial stability of said rotor so that said rotor axis remains substantially coextensive with said pump axis during operation;

permanent magnet means for establishing strong axial fields across said fluid gaps to provide radial stiffness and stability of said rotor during operation of the pump;

control means for maintaining axial stability of said rotor so that said rotor may absorb externally imposed axial loads and maintain said fluid gaps and axial separation between said rotor and said pump housing;

impeller means on said rotor operative to draw blood into said inlet opening and expel the blood through said outlet opening with rotation of said rotor;

drive means for rotating said rotor and impeller means thereby pumping blood; and blood washout means for continuously moving blood through said fluid gaps during rotation of said rotor to prevent formation of thrombus in said fluid gaps.

42. A blood pump to propel blood therethrough, comprising:

a pump housing defining a pump axis, and inlet and outlet openings in said pump housing;

a rotor defining a rotor axis and opposing rotor axial ends;

suspension means within said pump housing at said rotor axial ends for suspending said rotor for rotation within said housing and defining fluid gaps between said rotor axial ends and said suspension means and substantially maintaining the radial stability of said rotor so that said rotor axis remains substantially coextensive with said pump axis during operation;

control means for maintaining axial stability of said rotor so that said rotor may absorb externally imposed axial loads and maintain said fluid gaps and axial separation between said rotor and said pump housing;

impeller means on said rotor operative to draw blood into said inlet opening and expel the blood through said outlet opening with rotation of said rotor;

drive means for rotating said rotor and impeller means thereby pumping blood; and blood washout means for continuously moving blood through said fluid gaps during rotation of said rotor to prevent formation of thrombus in said fluid gaps, said rotor means comprising a generally cylindrical rotor housing having a cylindrical wall defining an axis coextensive with said rotor axis and an outer cylindrical surface forming, with said pump housing, an annular passageway for the blood in moving from said inlet to said outlet openings, and said impeller means comprises a plurality of axially directed helical blades mounted on at least an axial length of said outer cylindrical surface, said blades being substantially equally angularly spaced from each other about said rotor axis and said helical blades having a pitch and a length to at least partially circumferentially as viewed along said rotor axis to minimize back leakage.

43. A blood pump to propel blood therethrough, comprising:

a pump housing defining a pump axis, and inlet and outlet openings in said pump housing;

a rotor defining a rotor axis and opposing rotor axial ends;

suspension means within said pump housing at said rotor axial ends for magnetically suspending said rotor for rotation within said housing and defining fluid gaps between said rotor axial ends and said suspension means and substantially maintaining the radial stability of said rotor so that said rotor axis remains substantially coextensive with said pump axis during operation;

control means for maintaining axial stability of said rotor so that said rotor may absorb externally imposed axial loads and maintain said fluid gaps and axial separation between said rotor and said pump housing;

impeller means on said rotor operative to draw blood into said inlet opening and expel the blood through said outlet opening with rotation of said rotor;

drive means for rotating said rotor and impeller means thereby pumping blood; and blood washout means for continuously moving blood through said fluid gaps during rotation of said rotor to prevent formation of thrombus in said fluid gaps, said pump housings and impeller means being arranged to provide axial flow 0f blood, and further comprising tangential-to axial flow redirection means for redirecting the tangential flow of blood resulting from rotation of said impeller means to axial flow at said outlet end to eliminate flow separation turbulence at said outlet end.

44. A blood pump to propel blood therethrough, comprising:

a pump housing defining a pump axis, and inlet and outlet openings in of said pump housing;

a rotor defining a rotor axis and opposing rotor axial ends;

suspension means with in said pump housing at said rotor axial ends for suspending said rotor for rotation within said housing and defining fluid gaps between said rotor axial ends and said suspension means and substantially maintaining the radial stability of said rotor so that said rotor axis remains substantial coextensive with said pump axis during operation;

control means for maintaining axial stability of said rotor so that said rotor may absorb externally imposed axial loads and maintain said fluid gaps and axial separation between said rotor and said pump housing;

impeller means on said rotor operative to draw blood into said inlet opening and expel the blood through said outlet opening with rotation of said rotor;

drive means for rotating said rotor and impeller means thereby pumping blood; and blood washout means for continuously moving blood through said fluid gaps during rotation of said rotor to prevent formation of thrombus in said fluid gaps, said control means including arranged to detect variations in axial velocity of said rotor, and means for establishing differential pressure acting on said rotor on the basis of said velocity variations to provide physiological control of the pump responsive to a patient's heart rate, which is generally proportional to average differential pressures between systolic and diastolic blood pressures.

* * * * *

UNITED STATES PATENT AND TRADEMARK OFFICE
CERTIFICATE OF CORRECTION

PATENT NO.    : 6,527,699 B1
DATED         : March 4, 2003
INVENTOR(S)   : Michael Goldowsky It is certified that error appears in the above-identified patent and that said Letters Patent is hereby corrected as shown below:

<u>Column 6,</u>
Line 8, "0.10-inch" should be -- .010 inch --

Signed and Sealed this

Twenty-ninth Day of July, 2003

JAMES E. ROGAN
*Director of the United States Patent and Trademark Office*